United States Patent
Suo et al.

(10) Patent No.: US 9,422,360 B2
(45) Date of Patent: Aug. 23, 2016

(54) PORCINE CD28 RECEPTOR, GENE FOR ENCODING SAME, AND APPLICATION OF SAME

(75) Inventors: Xun Suo, Beijing (CN); Xianyong Liu, Beijing (CN); Huali Su, Beijing (CN); Xinxin Zhao, Beijing (CN); Xiaoxi Huang, Beijing (CN)

(73) Assignee: Zhonghao Chenguang Research Institute of Chemical Industry Company Limited, Fushun County Zigong, Sichuan (CN)

( * ) Notice: Subject to any disclaimer, the term of this patent is extended or adjusted under 35 U.S.C. 154(b) by 0 days.

(21) Appl. No.: 14/366,811

(22) PCT Filed: Dec. 19, 2011

(86) PCT No.: PCT/CN2011/002123
§ 371 (c)(1),
(2), (4) Date: Jul. 15, 2014

(87) PCT Pub. No.: WO2013/091130
PCT Pub. Date: Jun. 27, 2013

(65) Prior Publication Data
US 2015/0040254 A1 Feb. 5, 2015

(51) Int. Cl.
*A01N 63/00* (2006.01)
*A61K 48/00* (2006.01)
*C07K 14/705* (2006.01)
*A01K 67/027* (2006.01)
*C07K 16/28* (2006.01)

(52) U.S. Cl.
CPC ....... *C07K 14/70521* (2013.01); *A01K 67/0275* (2013.01); *C07K 16/2818* (2013.01); *A01K 2227/108* (2013.01); *C07K 2319/42* (2013.01)

(58) Field of Classification Search
None
See application file for complete search history.

(56) References Cited

U.S. PATENT DOCUMENTS 5,557,032 A * 9/1996 Mak .................................. 800/3

OTHER PUBLICATIONS

Rajagopalan et al. Intl Immunol 2002;14:801-12.*
Gogishvili et al. J Allergy Clin Immunol 2012;130:1394-403.*
Moreadith et al, J. Mol. Med., 1997;75(3):208-16.*
Pera et al., Journal of Cell Science 2000;113: 5-10.*
Denning, Nat Biotech 2001;19:559-562.*
Wilmut, Cloning Stem Cells 2003;5:99-100.*
Smith and Murphy, Cloning Stem Cells 2004;6:126-32.*
Polejaeva et al Nature 2000;407:86.*
Isono et al. Immunogenetics 1995;42:217-20.*
Pennesi et al. Hum Immunol 1999;60:291-304.*
Eck et al, 1995, Gene-Based therapy, book chapter.*
Deonarain, 1998, Expert Opin. Ther. Pat., vol. 8, pp. 53-69.*
Isono et al. Cloning and sequencing of the rabbit gene encoding T-cell costimulatory molecules. Immunogenetics 1995;42:217-220.*
GenBank [online], database accession No. XP_003133648.3 Oct. 11, 2011, see the sequence and related information.
Levine BL et al., Antiviral effect and ex vivo CD4+ T cell proliferation in HIV-positive patients as a result of CD28 costimulation, Science, Jun. 28, 1996, vol. 272, No. 5270 pp. 1939-1943, ISSN: 2225-7063, see the abstract.
Dawson HD et al., Identification of key Immune mediators regulating T helper 1 response in swine, Veterinary Immunology and Immunopathology, Jul. 31, 2004, vol. 100, No. 1-2, pp. 105-111, ISSN: 0165-2427, see the abstract, the last paragraph of the left column on p. 106 to the first paragraph of the right column on p. 109.
International Search Report for PCT/CN2011/002123.
Oreste, et al., Molecular modifiers of T cell antigen receptor triggering threshold: the mechanism of CD28 costimulatory receptor: Immunologic Reviews; 2003; vol. 192; pp. 21-31.
Bachmann; T cell responses are governed by avidity and co-stimulatory thresholds; Eur. J. Immunol: 1996; 26: pp. 2017-2022.
Zhao; High transfection efficiency of porcine peripheral blood T cells via nucleofection; Veterninary Immunology and immunopathology: 144; 2011; pp. 179-186.

* cited by examiner

*Primary Examiner* — Janice Li
(74) *Attorney, Agent, or Firm* — Stites & Harbison PLLC; Mandy Wilson Decker

(57) ABSTRACT

Provided is a porcine CD28 receptor molecule, which is: 1) a protein consisting of an amino acid sequence represented by SEQ ID NO:2, or 2) a protein derived from 1) by substitution, deletion or addition of one or several amino acids in the amino acid sequence represented by SEQ ID NO:2 and having equivalent activity with 1). Further provided is a gene for coding the porcine CD28 receptor, the nucleotide sequence of which is shown as SEQ ID NO:1. When the provided co-stimulating receptor CD28 is expressed specifically and highly in a T cell, the activation, proliferation and cell factor secretion activity of the T cell when stimulated by an antigen can be enhanced, thereby enhancing the acquired immune response of a host and enhancing the immune effect of a vaccine.

19 Claims, 4 Drawing Sheets

SEQUENCE LISTING

```
<160> NUMBER OF SEQ ID NOS: 26

<210> SEQ ID NO 1
<211> LENGTH: 1073
<212> TYPE: DNA
<213> ORGANISM: Unknown
<220> FEATURE:
<223> OTHER INFORMATION: Swine

<400> SEQUENCE: 1
acaatgcttc gtggtttgag tcccttgatc atgtgcccaa gggaagtaag tcgctggtgg       60
tagccgtggg tgacaagttg ctggggttca tctccagctc atctcacact tgggcttctc      120
```

-continued

| | |
|---|---|
| agggaggagg ggccggagcc ctggcccacc attcgcacaa tgatcctcgg gttactcctg | 180 |
| gctctcaact tcttcccctc aattcaagta acaggaaaca agattttggt gaagcagtcg | 240 |
| cccatacttg tggtgaacga caatgaggtc aaccttagct gcaagtacac ctacaacctc | 300 |
| ttctcaaagg agttccgggc atcccttat aagggagcag atagtgctgt ggaggtctgt | 360 |
| gttgtgaatg taaattactc ccgcctgctt cagtttaaac caaatacagg attcaactgc | 420 |
| gatgtgaagt atggcaacga aacagtgaca ttctacctcc ggaatttgca cgttaaccaa | 480 |
| acggatattt acttctgcaa aatcgaggtc ctgtatccgc ctccttatat agacaatgag | 540 |
| aagagtaacg ggactattat ccatgtgaaa gagaaacatt gtccagctcc tcggcctcct | 600 |
| gagtcttcta agatattttg ggtgctggtg gtggtaaatg gagtcgtagc tttctatagc | 660 |
| ttggtagtaa cattggctct ttttttctac tggatgaaga gtaagagaac caggatgctt | 720 |
| cagagtgact acatgaacat gacccccgc aggctggggc ccacccggaa gcactaccag | 780 |
| ccctatgcac cagcacgtga ctttgcagcc taccgctcct gacacggacg cctatccaga | 840 |
| tgcaggccgg ctggcacctc ttcacctgct caacaccact gctctggata ggaaaggact | 900 |
| gcctcatctt cagccagcca ccgcgggctc ctgttaagcc accagtgcca atatttctta | 960 |
| aacaactaga ctgaataaca tcattttgag actctgaagt gacattaaag aacgttactg | 1020 |
| tggcaggctc tatcttgtag tgccatggcc cagatgcaaa aaaaaaaaaa aaa | 1073 |

<210> SEQ ID NO 2
<211> LENGTH: 220
<212> TYPE: PRT
<213> ORGANISM: Unknown
<220> FEATURE:
<223> OTHER INFORMATION: Swine

<400> SEQUENCE: 2

Met Ile Leu Gly Leu Leu Leu Ala Leu Asn Phe Phe Pro Ser Ile Gln
1               5                   10                  15

Val Thr Gly Asn Lys Ile Leu Val Lys Gln Ser Pro Ile Leu Val Val
                20                  25                  30

Asn Asp Asn Glu Val Asn Leu Ser Cys Lys Tyr Thr Tyr Asn Leu Phe
            35                  40                  45

Ser Lys Glu Phe Arg Ala Ser Leu Tyr Lys Gly Ala Asp Ser Ala Val
        50                  55                  60

Glu Val Cys Val Val Asn Val Asn Tyr Ser Arg Leu Leu Gln Phe Lys
65                  70                  75                  80

Pro Asn Thr Gly Phe Asn Cys Asp Val Lys Tyr Gly Asn Glu Thr Val
                85                  90                  95

Thr Phe Tyr Leu Arg Asn Leu His Val Asn Gln Thr Asp Ile Tyr Phe
            100                 105                 110

Cys Lys Ile Glu Val Leu Tyr Pro Pro Tyr Ile Asp Asn Glu Lys
        115                 120                 125

Ser Asn Gly Thr Ile Ile His Val Lys Glu Lys His Cys Pro Ala Pro
130                 135                 140

Arg Pro Pro Glu Ser Ser Lys Ile Phe Trp Val Leu Val Val Val Asn
145                 150                 155                 160

Gly Val Val Ala Phe Tyr Ser Leu Val Val Thr Leu Ala Leu Phe Phe
                165                 170                 175

Tyr Trp Met Lys Ser Lys Arg Thr Arg Met Leu Gln Ser Asp Tyr Met
            180                 185                 190

-continued

```
Asn Met Thr Pro Arg Arg Leu Gly Pro Thr Arg Lys His Tyr Gln Pro
        195                 200                 205

Tyr Ala Pro Ala Arg Asp Phe Ala Ala Tyr Arg Ser
    210                 215                 220

<210> SEQ ID NO 3
<211> LENGTH: 22
<212> TYPE: DNA
<213> ORGANISM: Artificial Sequence
<220> FEATURE:
<223> OTHER INFORMATION: synthesized

<400> SEQUENCE: 3
atgctcaggc tgctcttggc tc                                          22

<210> SEQ ID NO 4
<211> LENGTH: 22
<212> TYPE: DNA
<213> ORGANISM: Artificial Sequence
<220> FEATURE:
<223> OTHER INFORMATION: synthesized

<400> SEQUENCE: 4
tcaggagcga taggctgcga ag                                          22

<210> SEQ ID NO 5
<211> LENGTH: 25
<212> TYPE: DNA
<213> ORGANISM: Artificial Sequence
<220> FEATURE:
<223> OTHER INFORMATION: synthesized

<400> SEQUENCE: 5
acattcacaa cacagacctc cacag                                       25

<210> SEQ ID NO 6
<211> LENGTH: 25
<212> TYPE: DNA
<213> ORGANISM: Artificial Sequence
<220> FEATURE:
<223> OTHER INFORMATION: synthesized

<400> SEQUENCE: 6
ggttgtaggt gtacttgcag ctaag                                       25

<210> SEQ ID NO 7
<211> LENGTH: 22
<212> TYPE: DNA
<213> ORGANISM: Artificial Sequence
<220> FEATURE:
<223> OTHER INFORMATION: synthesized

<400> SEQUENCE: 7
tggtggtggt aaatggagtc gt                                          22

<210> SEQ ID NO 8
<211> LENGTH: 22
<212> TYPE: DNA
<213> ORGANISM: Artificial Sequence
<220> FEATURE:
<223> OTHER INFORMATION: synthesized

<400> SEQUENCE: 8
gagtgactac atgaacatga cc                                          22
```

<210> SEQ ID NO 9
<211> LENGTH: 20
<212> TYPE: DNA
<213> ORGANISM: Artificial Sequence
<220> FEATURE:
<223> OTHER INFORMATION: synthesized

<400> SEQUENCE: 9
tcatcactaa gcaaggacgg                                          20

<210> SEQ ID NO 10
<211> LENGTH: 20
<212> TYPE: DNA
<213> ORGANISM: Artificial Sequence
<220> FEATURE:
<223> OTHER INFORMATION: synthesized

<400> SEQUENCE: 10
gaccacatcc acaaacatcc                                          20

<210> SEQ ID NO 11
<211> LENGTH: 21
<212> TYPE: DNA
<213> ORGANISM: Artificial Sequence
<220> FEATURE:
<223> OTHER INFORMATION: synthesized

<400> SEQUENCE: 11
gtcctcatct cttcaccttc c                                        21

<210> SEQ ID NO 12
<211> LENGTH: 21
<212> TYPE: DNA
<213> ORGANISM: Artificial Sequence
<220> FEATURE:
<223> OTHER INFORMATION: synthesized

<400> SEQUENCE: 12
cactctttct catcttgcct g                                        21

<210> SEQ ID NO 13
<211> LENGTH: 23
<212> TYPE: DNA
<213> ORGANISM: Artificial Sequence
<220> FEATURE:
<223> OTHER INFORMATION: synthesized

<400> SEQUENCE: 13
caagttctca gtcatgagaa cac                                      23

<210> SEQ ID NO 14
<211> LENGTH: 20
<212> TYPE: DNA
<213> ORGANISM: Artificial Sequence
<220> FEATURE:
<223> OTHER INFORMATION: synthesized

<400> SEQUENCE: 14
gagtaggcca cattacactg                                          20

<210> SEQ ID NO 15
<211> LENGTH: 20
<212> TYPE: DNA
<213> ORGANISM: Artificial Sequence
<220> FEATURE:
<223> OTHER INFORMATION: synthesized

```
<400> SEQUENCE: 15
ttccttccca gagttcttcc                                              20

<210> SEQ ID NO 16
<211> LENGTH: 22
<212> TYPE: DNA
<213> ORGANISM: Artificial Sequence
<220> FEATURE:
<223> OTHER INFORMATION: synthesized

<400> SEQUENCE: 16
ggtagatttc attgagtgtc ct                                           22

<210> SEQ ID NO 17
<211> LENGTH: 20
<212> TYPE: DNA
<213> ORGANISM: Artificial Sequence
<220> FEATURE:
<223> OTHER INFORMATION: synthesized

<400> SEQUENCE: 17
catcactatt ggcaacgagc                                              20

<210> SEQ ID NO 18
<211> LENGTH: 20
<212> TYPE: DNA
<213> ORGANISM: Artificial Sequence
<220> FEATURE:
<223> OTHER INFORMATION: synthesized

<400> SEQUENCE: 18
gacagcactg tgttggcata                                              20

<210> SEQ ID NO 19
<211> LENGTH: 28
<212> TYPE: DNA
<213> ORGANISM: Artificial Sequence
<220> FEATURE:
<223> OTHER INFORMATION: synthesized

<400> SEQUENCE: 19
gaattcatga tcctcgggtt actcctgg                                     28

<210> SEQ ID NO 20
<211> LENGTH: 55
<212> TYPE: DNA
<213> ORGANISM: Artificial Sequence
<220> FEATURE:
<223> OTHER INFORMATION: synthesized

<400> SEQUENCE: 20
ggatcctcaa gcaacgtccg gaacgtcgta cgggtaggag cggtaggctg caaag        55

<210> SEQ ID NO 21
<211> LENGTH: 20
<212> TYPE: DNA
<213> ORGANISM: Artificial Sequence
<220> FEATURE:
<223> OTHER INFORMATION: synthesized

<400> SEQUENCE: 21
ctaatcttcc aggtcactgc                                              20
```

```
<210> SEQ ID NO 22
<211> LENGTH: 21
<212> TYPE: DNA
<213> ORGANISM: Artificial Sequence
<220> FEATURE:
<223> OTHER INFORMATION: synthesized

<400> SEQUENCE: 22
cctccatgaa gtggtaaact c                                              21

<210> SEQ ID NO 23
<211> LENGTH: 21
<212> TYPE: DNA
<213> ORGANISM: Artificial Sequence
<220> FEATURE:
<223> OTHER INFORMATION: synthesized

<400> SEQUENCE: 23
gcaagtacct cagatgtacc t                                              21

<210> SEQ ID NO 24
<211> LENGTH: 20
<212> TYPE: DNA
<213> ORGANISM: Artificial Sequence
<220> FEATURE:
<223> OTHER INFORMATION: synthesized

<400> SEQUENCE: 24
ttgtcactct cctctttcca                                                20

<210> SEQ ID NO 25
<211> LENGTH: 20
<212> TYPE: DNA
<213> ORGANISM: Artificial Sequence
<220> FEATURE:
<223> OTHER INFORMATION: synthesized

<400> SEQUENCE: 25
ctcaacggga agctcactgg                                                20

<210> SEQ ID NO 26
<211> LENGTH: 24
<212> TYPE: DNA
<213> ORGANISM: Artificial Sequence
<220> FEATURE:
<223> OTHER INFORMATION: synthesized

<400> SEQUENCE: 26
tgatgtcatc atattttgca ggtt                                           24
```

PORCINE CD28 RECEPTOR, GENE FOR ENCODING SAME, AND APPLICATION OF SAME

CROSS REFERENCE TO RELATED APPLICATIONS

This application is a §371 national stage application of PCT/CN2011/002123 filed Dec. 19, 2011.

TECHNICAL FIELD

The invention is directed to the field of animal genetic engineering, in particular to porcine CD28 receptor, gene encoding the same and the use of the same.

BACKGROUND

China is a major producer and consumer of pork. However, the epidemic diseases, such as swine fever and porcine reproductive and respiratory syndrome (Blue-eared Disease, PRRSV), are currently widely spread, which is the greatest difficulty that China's swine industry is facing. The prevention and control of these diseases are thus a major issue to be addressed for the stability and development of swine industry. However, in recent years, the diseases in a swine tend to evolve into multi-pathogen cross-infection, and disease resistance of swine and control effect of a vaccine are significantly reduced. Therefore, for better prevention and control of the diseases, it is required to find new strategies for development of a vaccine or to seek alternative or auxiliary approaches, such as breeding of new varieties of the swine with disease resistance. However, a lot of prior researches have been dedicated to breeding new varieties of livestock with single disease resistance using a specific disease resistance gene, there is thus clearly a large gap for such strategy to satisfy the current reality of frequent occurrence of disease in China's swine industry. Therefore, it becomes the ideal of many researchers that new varieties of the swine with broad-spectrum disease resistance are bred.

Adaptive immune response plays a crucial role in resisting invasion of pathogen by an animal. The activation of T cells is the top priority of the response. Recent studies have shown that effective activation of the T cells requires a two-signal stimulation. One is the signal generated by the binding of the MHC-peptide to TCR, and the other is the second signal generated by the binding of co-stimulatory receptor, primarily CD28, to its ligand. In a normal micro-environment of organism, the antigen-presenting cells often present a small number of antigenic peptides, the binding of which to TCR is not sufficient to activate T cells, thereby causing response impotence of T cells. The co-stimulatory signal pathway provided by T cell co-stimulatory receptors such as CD28 can compensate weaker TCR signaling, thereby activating T cells. Furthermore, when the affinity of TCR with antigen peptides is not sufficient, it is often difficult to activate T cells. The adequate co-stimulatory signals can also play the role of enhancing TCR signaling pathway, so as to activate T cells. In short, sufficient co-stimulatory signals can not only overcome the problem of low rate occupation of TCRs, but also compensate the inadequate TCR affinity. Therefore, co-stimulatory receptor-mediated signaling can enhance the function of adaptive immune system, so that the co-stimulatory receptor becomes a potential candidate for broad-spectrum disease resistance gene.

The gene sequence information and protein function of CD28 receptor, as a typical representative of co-stimulatory receptors, are already described in detail in studies in human and mice. CD28 receptor is recognized as a main co-stimulatory molecule for the initial proliferation and survival of T cells. The receptor can significantly promote activation, proliferation and survival of T cells and can affect the direction of T cell differentiation and up-regulate the expression of cytokines such as IFN-γ when it is linked to its ligand B7.1 (also called CD80) or B7.2 (also called CD86). It has been found that the level of expression of CD28 molecule is significantly down-regulated on the surface of T cells of the aged, and low level of expression of CD28 molecule is also found in some cases of delayed immune system activation. Thus, the expression level of the CD28 molecule directly affects the effective activation of immune system, thereby affecting the disease resistance of the individual organism.

CD28 receptor plays an important role in establishing, enhancing and maintaining T cell immune response, which indicates that CD28 receptor, as a target gene, has good prospects in transgenic breeding research and application. However, the vast majority of relevant studies on co-stimulatory molecules are based on the manner of gene knockout, or removal or enhancement of co-stimulatory signals using anti-CD28 monoclonal antibody. These strategies are obviously unsuitable for breeding research. Furthermore, only predicted genetic sequence information of porcine CD28 receptor is currently published, but its precise coding sequence and protein function haven't been reported so far.

SUMMARY

The object of the present invention is to provide a porcine CD28 receptor, a gene encoding the same, and the application of the same.

To achieve the mentioned object, the present invention firstly provides a porcine CD28 receptor, which is a protein consisting of the amino acid sequence represented by SEQ ID NO. 2.

It should be understood that a person skilled in the art will be able to obtain the mutated sequence of said protein by substitution, deletion and/or addition of one or more amino acids according to the amino acid sequence disclosed by the present invention without affecting the activity. Accordingly, the porcine CD28 receptor of the present invention further comprises a protein derived from the protein consisting of the amino acid sequence represented by SEQ ID NO. 2 by substitution, deletion or addition of one or more amino acids in the amino acid sequence of SEQ ID NO. 2 and having an activity equivalent with the protein consisting of the amino acid sequence represented by SEQ ID NO. 2. For example, in non-reactive region, the serine at position 181 is replaced by threonine, the glutamine at position 188 is deleted, or three prolines are added after position 198.

Preferably, the amino acid sequence of the derived protein has a homology of more than 70%, preferably more than 80%, more preferably more than 90% with the amino acid sequence represented by SEQ ID No.2.

The present invention also provides a gene encoding the above proteins. Preferably, the gene encoding porcine CD28 receptor provided by the present invention has a nucleotide sequence as shown in SEQ ID No. 1.

It should be understood, considering the degeneracy of codons and the codon preference of different species, that a person skilled in the art may use an appropriate species-specific codon as required.

The present invention also provides a vector, cell lines and host bacteria containing the porcine CD28 receptor gene, all of which are encompassed in the present invention.

The present invention further provides the use of the porcine CD28 receptor for improvement of broad-spectrum disease resistance. For example, after oral or injection administration of the biological agent developed by preparation of anti-porcine CD28 monoclonal antibody, the binding of this antibody to CD28 receptor can enhance the second signal required by T cell activation, and thereby enhancing T-cell immune response and improving disease resistance of a swine.

The present invention also provides the use of said porcine CD28 receptor gene for breeding swine with broad-spectrum disease resistance. The specific process includes:

1) cloning a porcine CD28 receptor gene into an eukaryotic expression vector, or obtaining porcine CD28 receptor gene mRNA by transcription in vitro;

2) introducing the prepared recombinant vector or mRNA into a porcine embryonic cell by electroporation; and 3) obtaining a transgenic swine with improved resistance against broad-spectrum diseases due to the up-regulation of CD28 expression level.

The transgenic strategy, which is based on co-stimulatory receptor CD28 of the invention, is a novel strategy for animal breeding research. The CD28 co-stimulatory receptor is specifically and highly expressed in T cells. The CD28 co-stimulatory receptor can enhance the activation and proliferation of T cells and cytokine secretion activity when T cells are stimulated by an antigen, thereby enhancing the acquired immune response of a host and enhancing immune effect of a vaccine. Thus, it can be anticipated by a person skilled in the art that the bred transgenic animal individual has significantly increased immune function and disease resistance against pathogen infection. The strategy based on high expression of CD28 can more effectively enhance disease resistance of the host against multi-pathogen cross-infection and improve vaccine efficacy in comparison with a new variety of livestock with single disease resistance.

DETAILED DESCRIPTION OF THE INVENTION

Figure 1:
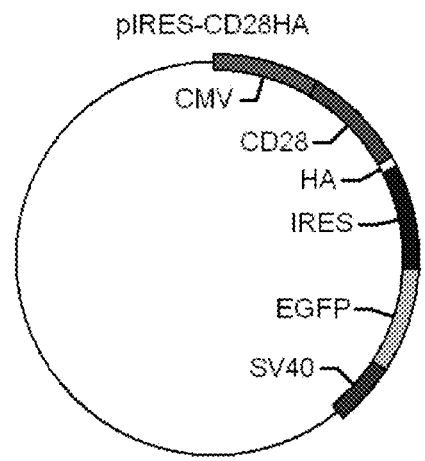
FIG. 1 is a map of construction of vector pIRES-CD28HA, wherein CMV refers to cytomegalovirus (CMV) promoter, a promoter that can regulate the expression of gene of interest in eukaryotic cell; CD28 refers to porcine CD28 gene coding region; HA refers to a segment of gene sequence encoding one HA (influenza virus hemagglutinin epitope) short peptide, which can be used as a label to detect the expression of fusion protein; IRES refers to a short segment of RNA sequences at eukaryotic mRNA 5' terminal, which can independently initiate translation; EGFP refers to an enhanced green fluorescent protein coding region; SV40 refers to a segment of polyA denosine residues at the terminal of Simian vacuolating virus 40 mRNA, which play a role in transcription termination and enhancement of RNA stability.

The following examples will be used to illustrate the present invention but are not intended to limit the scope of the present invention.

EXAMPLE 1

Cloning of CD28 Gene

On the theoretical basis that human gene sequences have a high similarity to porcine gene sequences by alignment, the primer is designed according to the human CD28 sequence, and the suspected porcine CD28 sequence is obtained using cDNA of wuzhishan pig (WISP) as a template. The specific steps are as follows:

(1) obtaining the gene fragments with high similarity from porcine genome by alignment with the human CD28 gene sequences, and designing the primers based on these gene fragments (see. Table 1: P1 and P2), (2) Extracting cDNA from porcine peripheral blood mononuclear cells (PBMC):

20 ml blood is collected sterilely from porcine anterior vena cava with heparin as anticoagulant, diluted with an equal volume of PBS, mixed uniformly and added slowly into equal volume of porcine lymphocyte separation medium (Tianjin Hap Xiang, China), and then centrifuged with horizontal rotor at 1800 rpm for 20 min. PBMC is obtained by extracting the lymphocyte layer of plasma. Total RNA of PBMC is extracted using Trizol reagent (TRIzol®LS Reagent) purchased from Invitrogen, then porcine cDNA is synthesized by reverse transcription kit (First Strand Synthesis Kit for RT-PCR) of ABI.

(3) The suspected sequence of CD28 is amplified using porcine cDNA as a template via phusion fidelity polymerase kit purchased from NEB.

Amplification reaction system: double distilled water. 34.5 µl; 5× HP buffer. 10 µl; 10 mM dNTP mix, 1 µl; 25 µM P1, 1 µl; 25 µMP2, 1 µl; phusion polymerase, 0.5 µl; cDNA, 2 µl.

Reaction procedure: pre-denaturation: 98° C., 1 min; cycle(35): 98° C., 10 s; 55° C., 20 s; 72° C., 1 min; supplementary extension: 72° C., 10 min.

The resulting amplified product is ligated to a commercial cloning vector (pEASY-Blunt Simple) for sequencing by Shanghai Meiji Bio-Pharmaceutical Co., Ltd.

(4) The primers required for 5'RACE and 3RACE are designed according to the sequence information obtained in step (3) (Table 1: 5'GSP1 and 5'GSP2; 3'GSP1 and 3'GSP2). The sequence information of 5' and 3' terminal transcribed untranslated region (UTR) is obtained using kit (5'-Full RACE Kit and 3'-Full RACE Core Set Ver.2.0) purchased from TAKARA. cDNA full-length sequence is represented by SEQ ID No. 1 and the full-length amino acid sequence of the protein is represented by SEQ ID No. 2.

body (Anti-murine CD3e, BD) is diluted with PBS (PH7.2-7.4) to 2 µg/ml, and B7 molecule (recombinant B7-1/Fc chimeric protein (R&D Systems, Minneapolis, Minn.)) is also diluted with PBS (pH7.2-7.4) to 0.4 µg/ml. 50 µl of the diluted anti-CD3 antibody and B7 molecule are added into each well, respectively. The plate is incubated at 4° C. overnight. T cells may be added into the wells after washed with PBS twice.

(4) Extraction of murine splenic T cells. The extraction of murine splenic T cells is performed in accordance with the instruction of Pan T Cell Isolation Kit from Miltenyi Biotec.

(5) Transfection of murine splenic T cells. The isolated $2\times10^6$ T cells is dissolved in 100 µl murine T cell transfection solution (Nucleofector® Solution, AMAXA), and 20 µg CD28 mRNA is added thereto. The negative control is prepared, in which no RNA is added. The samples are mixed gently and transferred into 2 mm nucleofector cuvet (AMAXA). The cuvet is putted into nucleofector(AMAXA) and the transfection is performed with X001 transfection procedure, and then 0.5 ml of complete 1640 medium preheated at 37° C. are rapidly added, and the cells are stimulated

TABLE 1

Primers used for cloning of porcine CD28 gene

| Application | Primers' names | Sequences of primers |
|---|---|---|
| Preliminary amplification of porcine CD28 sequence | P1 | 5' ATGCTCAGGCTGCTCTTGGCTC 3' (SEQ ID NO: 3) |
| | P2 | 5' TCAGGAGCGATAGGCTGCGAAG 3' (SEQ ID NO: 4) |
| 5'RACE | 5'GSP1 | 5' ACATTCACAACACAGACCTCCACAG 3' (SEQ ID NO: 5) |
| | 5'GSP2 | 5' GGTTGTAGGTGTACTTGCAGCTAAG 3' (SEQ ID NO: 6) |
| 3'RACE | 3'GSP1 | 5' TGGTGGTGGTAAATGGAGTCGT 3' (SEQ ID NO: 7) |
| | 3'GSP2 | 5' GAGTGACTACATGAACATGACC 3' (SEQ ID NO: 8) |

EXAMPLE 2

Influence of Up-regulation of Expression of CD28 Gene on T Cell Immune Response in Mouse Model BALB/C mouse system is used as a model to detect the change of its cellular functions after over-expression of CD28. The specific steps are as follows:

(1) Construction of plasmid pGEM4Z/mCD28/A64: plasmid pGEM4Z/mCD28/A64 is constructed using pGEM4Z (purchased from Promega) as the starting vector according to the method disclosed in David Boczkowski, Smita K. Nair, Jong-Hee Nam, et al., Induction of Tumor Immunity and Cytotoxic T Lymphocyte Responses Using Dendritic Cells Transfected with Messenger RNA Amplified from Tumor Cells, 2000.

(2) Synthesis and purification of CD28 mRNA: CD28 mRNA is synthesized in accordance with the instruction of RiboMAX™ Large Scale RNA Production Systems-T7 from Promega. The synthesized CD28 mRNA is purified by kit RNessy Mini Kit (Qiagen) and dissolved in DEPC water, followed by measuring its concentration by spectrophotometer, and then subpackaging and storing it at −80° C.

(3) Simulation of establishment of antigen presenting system (i.e., a 96-well plate for cell culture is coated with anti-CD3 antibody and B7 molecules). The anti-murine CD3 antiby adding them onto the cell culture plate coated with anti-CD3 antibody and B7 molecules (approximately $0.7\times10^6$ cells/well). The cell culture plate is cultured at 37° C. in a 5% $CO_2$ incubator.

(6) Detection of CD28 expression level in transfected murine splenic T cells. The transfected T cells are stimulated by simulated antigen-presenting system (CD3 antibody and B7 molecule -coating system) for 24 hours and stained with APC-labelled anti-murine CD28 antibody (Biolegend). The expression level of CD28 is detected by flow cytometry.

(7) Detection of activation of transfected murine splenic T cells when stimulated by antigen-presenting system. The transfected T cells are stimulated by simulated antigen-presenting system (CD3 antibody and B7 molecule-coating system) for 24 hours, and then stained with FITC-labelled anti-murine CD25 antibody, APC-labelled anti-murine CD44 antibody and PerCP/Cy5.5 labelled anti-murine CD69 antibody (Biolegend). The expression level of activation makers such as CD25, CD44 and CD69 are detected by flow cytometry.

(8) Detection of secretion of cytokines (IFN-γ and IL-4) in the transfected murine splenic T cells when stimulated by antigen-presenting system. The transfected T cells are stimulated by simulated antigen-presenting system (CD3 antibody and B7 molecule-coating system) for 48 hours. The supernatant of the cell culture is collected. The quantitative analysis for secreted cytokines is performed by ELISA. IFN-γ is measured by reference to the instruction of Mouse IFNλ ELISA kit from eBioscience. IL-4 is measured by reference to the instruction of Rat Anti-Mouse Interleukin-4 (IL-4) ELISA Set from SouthernBiotech.

(9) Detection of differentiation direction of transfected murine splenic T cells when stimulated by antigen-presenting system. The transfected T cells are stimulated by simulated antigen-presenting system (CD3 antibody and B7 molecule-coating system) for 48 hours. RNA of the cells is extracted and the reverse transcription is carried out. The transcriptional levels of transcription factors such as T-bet, GATA3, RORγt and Foxp3 are analyzed by relative fluorescence quantitative PCR (SYBGreen dye method) using Beta-Actin gene as a reference gene. The primers used in the reaction are shown in Table 2 below.

TABLE 2

The primers used in the analysis of the transcriptional level of mouse individual transcription factors by relative fluorescence quantitative PCR. (SYBGreen dye method)

| Genes | Upstream primers | Downstream primers |
|---|---|---|
| T-bet | 5' TCATCACTAAGCAAGGACGG 3' (SEQ ID NO: 9) | 5' GACCACATCCACAAACATCC 3' (SEQ ID NO: 10) |
| Gata3 | 5' GTCCTCATCTCTTCACCTTCC 3' (SEQ ID NO: 11) | 5' CACTCTTTCTCATCTTGCCTG 3' (SEQ ID NO: 12) |
| RORγt | 5' CAAGTTCTCAGTCATGAGAACAC 3' (SEQ ID NO: 13) | 5' GAGTAGGCCACATTACACTG 3' (SEQ ID NO: 14) |
| Foxp3 | 5' TTCCTTCCCAGAGTTCTTCC 3' (SEQ ID NO: 15) | 5' GGTAGATTTCATTGAGTGTCCT 3' (SEQ ID NO: 16) |
| Beta-Actin | 5' CATCACTATTGGCAACGAGC 3' (SEQ ID NO: 17) | 5' GACAGCACTGTGTTGGCATA 3' (SEQ ID NO: 18) |

Figure 2:
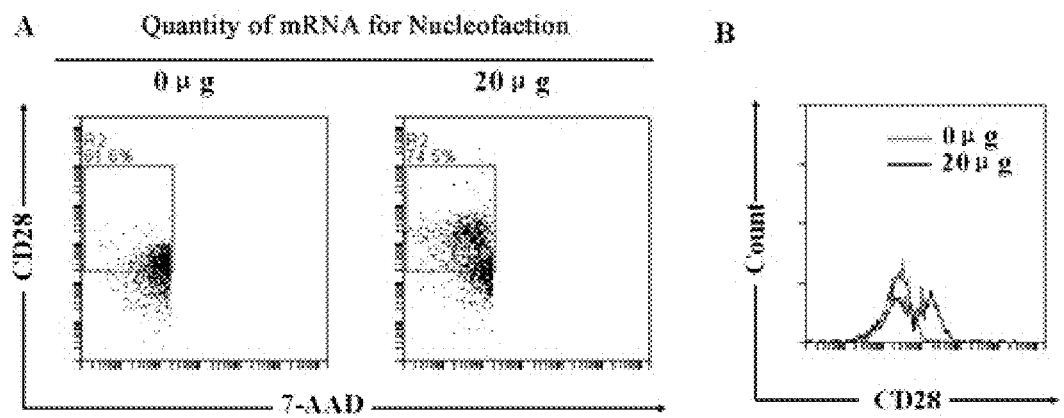
FIG. 2 shows the high expression of CD28 detected by flow cytometry after murine T cells are transfected with murine CD28 mRNA, wherein panel A shows increased numbers of T cells highly expressing CD28 after transfection with 20μg CD28 mRNA; and panel B shows that T cells highly expressing CD28 have an increased fluorescence intensity, namely the average number of CD28 molecule on the surface of each T cell is increased.
Figure 3:
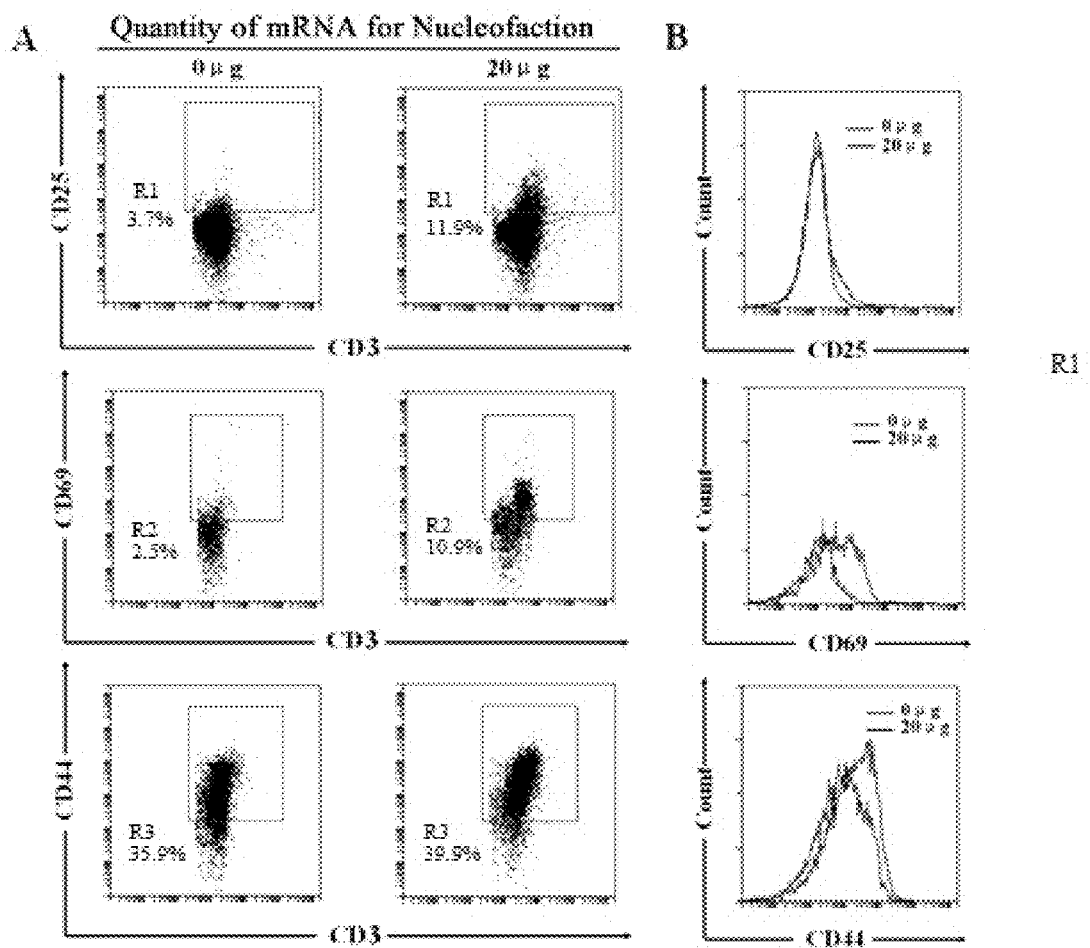
FIG. 3 shows murine T cells transfected with murine CD28 mRNA present up-regulated expression level of activation marker molecule (Marker) after stimulation by antigen-presenting system, wherein panel A shows increased numbers of T cells highly expressing the activation marker (CD25, CD44 and CD69) after transfection with 20 μg CD28 mRNA; and panel B shows that T cells highly expressing the activation marker (CD25, CD44 and CD69) have an increased fluorescence intensity, namely the average number of CD28 molecule on the surface of each T cell is increased.
Figure 4:
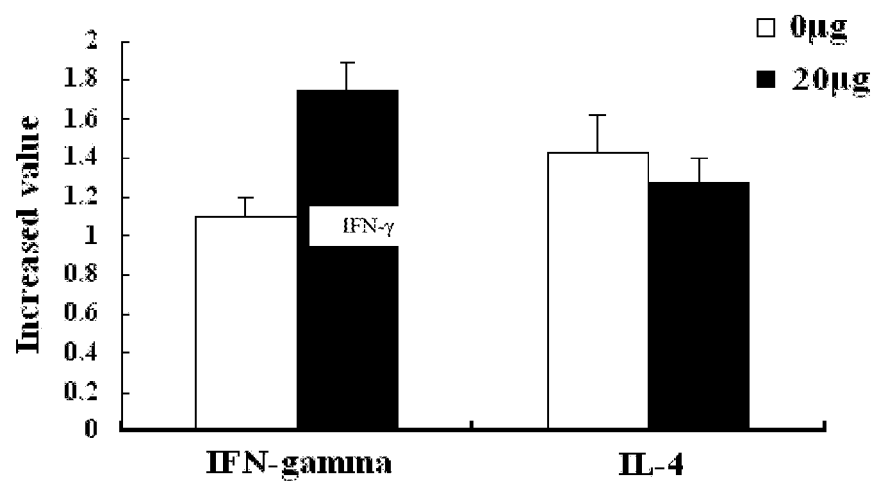
FIG. 4 shows murine T cells transfected with murine CD28 mRNA present increased secretion of IFN-γ after stimulation by antigen-presenting system, but the secretion of IL-4 does not change significantly as compared to the cells un-transfected with CD28 mRNA.
Figure 5:
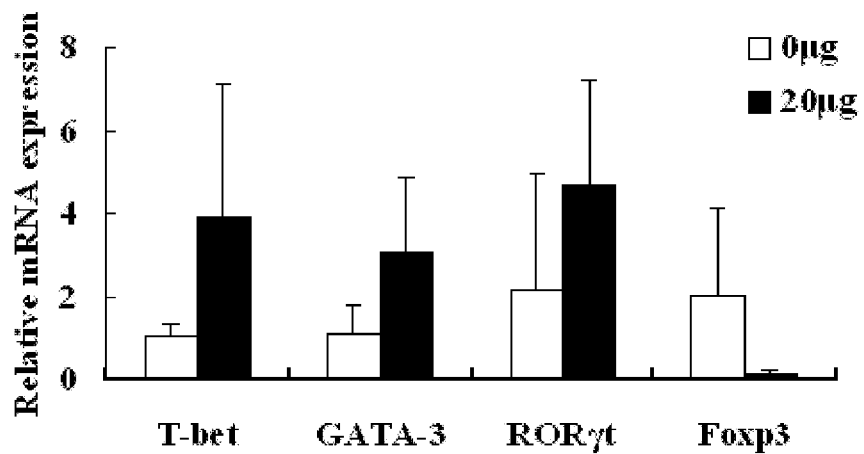
FIG. 5 shows that the cell differentiation direction of murine T cells transfected with murine CD28 mRNA is significantly affected after stimulation by antigen-presenting system, wherein the up-regulation of transcription factors T-bet, GATA3, and RORyt indicates that more T cells are differentiated into Th1, Th2 and TM7 that are subtypes having a role of positive immune regulation, and the down-regulation of Foxp3 factor indicates that the differentiation of T cells into Treg (negative regulation) is suppressed.

The results indicate that, after transfection with mRNA, the number of T cells showing high-APC fluorescence intensity is significantly increased, which means that the expression of CD28 is significantly up-regulated (FIG. 2). When T cells highly expressing CD28 are stimulated by antigen-presenting system, the expression of the activation marker molecules CD25, CD44 and CD69 on cell surface is significantly up-regulated (FIG. 3). It can be seen from ELISA results that, when T cells transfected with CD28 mRNA are stimulated, the secretion activity of cytokine IFN-γ is significantly enhanced in these cells (FIG. 4). Moreover, according to the detection result of transcriptional level, the expression levels of the transcription factors T-bet (Th1 type), GATA3 (Th2 type), RORγt (Th17 type) are significantly up-regulated, indicating that the tendency of differentiation of T cells into Th1, Th2 and Th17 which are subtypes having positive immune regulation is increased (FIG. 5).

EXAMPLE 3

Influence of the Up-regulated Expression of Porcine CD28 Gene on T Cell Immune Response According to the strategy provided by the present invention, porcine peripheral blood mononuclear cells (PBMC, essentially comprising T lymphocytes) are transfected with plasmids containing porcine CD28 gene, and the cell activation and the secretion activity of cytokines are detected at a cellular level when the transfected cells are stimulated by the antigen (PRRSV).

(1) Construction of eukaryotic expression vector pIRES-CD28HA. Upstream primer: 5' (EcoRI)GAATTCATGATC-CTCGGGTTACTCCTGG 3' (SEQ ID NO: 19) and downstream primer: 5' (BamHI)GGATCCTCAAGCAACG-TCCGGAACGTCGTACGGGTAGGAGCGGTAGGCTG-CAAAG 3' (SEQ ID NO: 20)(the shaded portion is HA tag sequence) are designed and the fragment of porcine CD28 is amplified using the cloning vector containing CD28 gene as a template. The reaction system and procedure are the same as in Step 3 of Example 1. The cloned fragments contain EcoRI and BamHI enzyme cleavage sites at both ends thereof respectively, and the HA tag sequence is introduced downstream thereof to facilitate the detection of expression of fusion protein by western-blot. Finally, the resulting amplified fragment is ligated to backbone vector pIRES2-EGFP (purchased from BD Biosciences Clontech) co-digested by EcoRI and BamHI. The constructed plasmid is shown in FIG. 1.

(2) Massive extraction of pIRES-CD28HA plasmid:

pIRES-CD28HA plasmids are massively extracted according to the instruction of E.Z.N.A.™ Endo-Free Plasmid Maxi Kit produced by OMEGA. After plasmid extraction, the concentration of the plasmid is measured by a spectrophotometer.

(3) Extraction of porcine peripheral blood mononuclear cells (PBMC):

20 ml blood is collected sterilely from porcine anterior vena cava with heparin as anticoagulant, diluted with an equal volume of PBS, mixed uniformly and added slowly into equal volume of porcine lymphocyte separation medium (Tianjin Hao Xiang, China), and then centrifuged with horizontal rotor at 1800 rpm for 20 min. PBMC is obtained by extracting the lymphocyte layer of plasma.

(4) Transfection of porcine PBMC:

After cell counting, $5 \times 10^6$ PMBC are dissolved in 100 μl of mouse lymphocyte transfection buffer (AMAXA, mouse T cell transfection kit) which has returned to room temperature, and 4 μg pIRES-CD28HA is added thereto. The negative group is also established, in which no plasmid is added. The samples are mixed gently and transferred into 2 mm nucleofector cup (AMAXA). The cup is putted into the nucleofector (AMAXA) and the transfection is performed with inherent procedure Z001, and then the cells are rapidly transferred into 2 ml of complete 1640 medium preheated at 37° C., and cultured in a 5% $CO_2$ incubator at 37° C.

(5) Detection of expression of exogenous genes by Eestem-blot. Vector pIRES-CD28HA used for transfection bears CD28 gene that has fused with HA tag, the commercial antibody with mouse anti-HA tag can be used to hybrid with fusion protein, then anti-mouse secondary antibody labelled with HRP (horseradish peroxidase) is used to detect the hybridization.

(6) Detection of activation of transfected porcine peripheral blood mononuclear cells (PBMC) when stimulated by the antigen (PRRSV). Porcine PBMC is transfected with vector pIRES-CD28HA for 8 hours, followed by infection with 0.1 MOI PRRSV. After 24 hours from infection, the transcriptional level of T cell activation Marker CD25 molecule is analyzed by relative fluorescence quantitative PCR (SYBGreen dye method) with GAPDH gene as the reference gene. The used primers are shown in Table 3 below.

TABLE 3 the primers used in the analysis of the transcriptional level of porcine activation Marker (CD25 molecule) and IFN-γ by relative fluorescence quantitative PCR (SYBGreen dye method)

| Genes | Upstream primers | Downstream primers |
|---|---|---|
| CD25 | 5' CTAATCTTCCAGGTCACTGC 3' | 5' CCTCCATGAAGTGGTAAACTC 3' |
| IFN-γ | 5' GCAAGTACCTCAGATGTACCT 3' | 5' TTGTCACTCTCCTCTTTCCA 3' |
| GAPDH | 5' CTCAACGGGAAGCTCACTGG 3' | 5' TGATGTCATCATATTTTGCAGGTT 3' |

(7) Detection of transcriptional level of IFN-γ in the transfected porcine peripheral blood mononuclear cells (PBMC) when stimulated by the antigen (PRRSV). Porcine PBMC is transfected with vector pIRES-CD28HA for 8 hours, followed by infection with 0.1MOI PRRSV. After 24 hours from infection, the transcriptional level of IFN-γ is analyzed by relative fluorescence quantitative PCR (SYBGreen dye method) with GAPDH gene as the reference gene.

Figure 6:
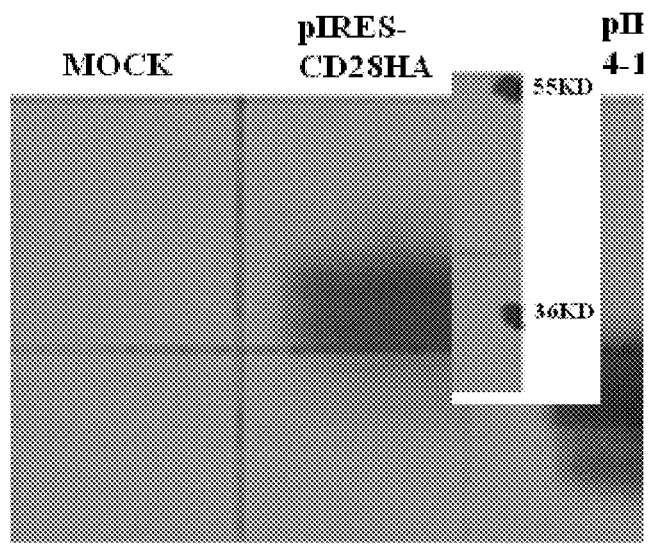
FIG. 6 shows the detection of the expression of heterologous proteins in the porcine peripheral blood mononuclear cells (PBMC) transfected with plasmid pIRES-CD28HA by Western blot.
Figure 7:
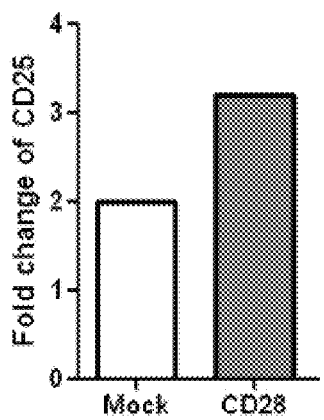
FIG. 7 shows that the transcription level of T-cell activation marker CD25 molecule of a porcine peripheral blood mononuclear cells (PBMC) transfected with plasmid pIRES-CD28HA is significantly increased when stimulated by an antigen (PRRSV).
Figure 8:
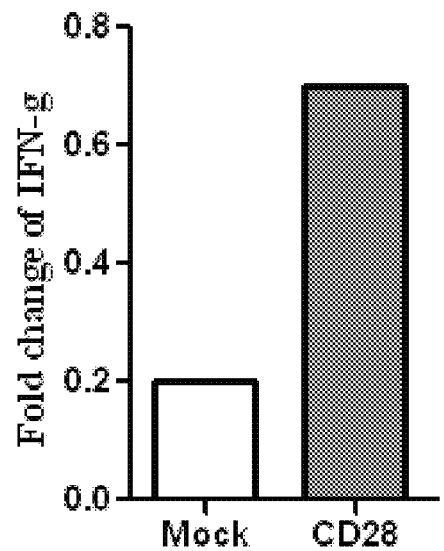
FIG. 8 shows that the transcription level of IFN-γ of a porcine peripheral blood mononuclear cells (PBMC) transfected with plasmid pIRES-CD28HA is significantly increased when stimulated by an antigen (PRRSV).
Figure 8:
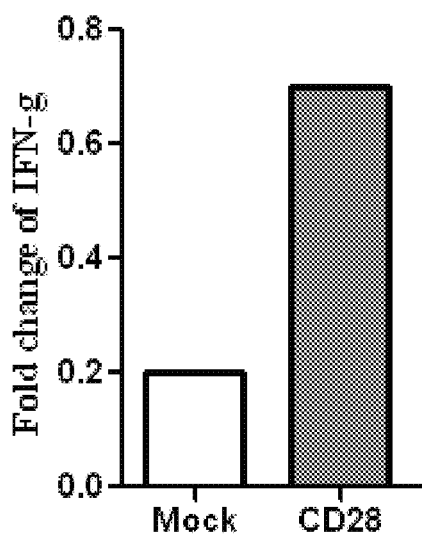

The results are shown in the drawings. The fusion protein may be successfully expressed in the porcine PBMC cells transfected with vector pIRES-CD28HA (FIG. 6) by detection with anti-HA monoclonal antibody. After PBMC cells highly expressing CD28 (FIG. 7) are stimulated by the antigen-presenting cells infected with PRRSV, the transcriptional level of activation Marker molecule CD25 is significantly up-regulated and the transcriptional level of cytokine IFN-γ in activated PBMC is also significantly increased (FIG. 8).

INDUSTRIAL APPLICABILITY

The present invention provides co-stimulatory receptor CD28 that is specifically and highly expressed in T cells. The co-stimulatory receptor CD28 can enhance activation, proliferation and cytokine secretion activity of T cells when they are stimulated by an antigen, thereby enhancing acquired immune response of a host and the immune effect of a vaccine.

What is claimed is:

1. A method of enhancing an immune response in a host cell, comprising:
   administering to the cell
   a polypeptide comprising the amino acid sequence of SEQ ID NO: 2 or a mutant thereof, or
   a polynucleotide comprising a nucleic acid sequence encoding the amino acid sequence of SEQ ID NO: 2 or a mutant thereof; or
   a polynucleotide comprising the nucleic acid sequence of SEQ ID NO: 1.

2. A method of preparing a CD28 antibody, comprising administering to a rodent a polypeptide comprising the amino acid sequence of SEQ ID NO: 2 to induce a specific immune response to the polypeptide, and preparing antibodies generated by the immune response in the rodent.

3. The method of claim 1, wherein the cell is a T-lymphocyte.

4. The method of claim 1 wherein the cell is a peripheral blood mononuclear cell.

5. The method of claim 1, wherein the mutant of SEQ ID NO: 2 has a homology of more than 90% with the amino acid sequence of SEQ ID NO: 2.

6. The method of claim 1, wherein the mutant of SEQ ID NO: 2 comprises the amino acid sequence of SEQ ID NO: 2 wherein the serine at position 181 is replaced by threonine.

7. The method of claim 1, wherein the mutant of SEQ ID NO: 2 comprises the amino acid sequence of SEQ ID NO: 2 wherein three prolines are added after position 198.

8. The method of claim 1, wherein the mutant of SEQ ID NO: 2 comprises the amino acid sequence of SEQ ID NO: 2 wherein the glutamine at position 188 is deleted.

9. The method of claim 1, wherein the polynucleotide is provided in a vector.

10. The method of claim 9, wherein the vector is pIRES.

11. The method of claim 1, wherein the cell is in a porcine animal.

12. The method of claim 11, wherein administration results in an enhanced immune response to a porcine RNA virus.

13. The method of claim 12, wherein the virus is porcine reproductive and respiratory syndrome virus.

14. The method of claim 1, wherein the enhanced immune response is measured by an increased transcription of CD25 in the cell.

15. The method of claim 1, wherein the enhanced immune response is measured by an increased transcription of cytokines in the cell.

16. A cDNA molecule, comprising the nucleic acid sequence of SEQ ID NO: 1.

17. A vector comprising the cDNA molecule of claim 16.

18. A cell comprising the vector of claim 17.

19. A cell of claim 18 wherein the cell is a porcine peripheral blood mononuclear cell.

\* \* \* \* \*